(12) United States Patent
Purandare et al.

(10) Patent No.: US 9,402,854 B2
(45) Date of Patent: Aug. 2, 2016

(54) PHARMACEUTICAL COMPOSITION

(71) Applicant: Cipla Limited, Mumbai (IN)

(72) Inventors: Shrinivas Purandare, Mumbai (IN); Geena Madhukar Malhotra, Mumbai (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 14/389,684

(22) PCT Filed: Apr. 10, 2013

(86) PCT No.: PCT/GB2013/000161
§ 371 (c)(1),
(2) Date: Sep. 30, 2014

(87) PCT Pub. No.: WO2013/153349
PCT Pub. Date: Oct. 17, 2013

(65) Prior Publication Data
US 2015/0080358 A1    Mar. 19, 2015

(30) Foreign Application Priority Data
Apr. 11, 2012 (IN) .................. 1179/MUM/2012

(51) Int. Cl.
*A61K 31/56* (2006.01)
*A61K 31/58* (2006.01)
*A61K 9/00* (2006.01)
*A61K 31/167* (2006.01)
*A61K 45/06* (2006.01)

(52) U.S. Cl.
CPC ............... *A61K 31/58* (2013.01); *A61K 9/008* (2013.01); *A61K 9/0075* (2013.01); *A61K 31/167* (2013.01); *A61K 45/06* (2013.01)

(58) Field of Classification Search
USPC ....................................... 514/171
See application file for complete search history.

(56) References Cited

U.S. PATENT DOCUMENTS

| | | | |
|---|---|---|---|
| 6,030,604 A | 2/2000 | Trofast | |
| 6,150,418 A * | 11/2000 | Hochrainer et al. | 514/630 |
| 6,458,338 B1 * | 10/2002 | Adjei et al. | 424/46 |
| 7,172,752 B2 | 2/2007 | Watanabe et al. | |
| 2005/0053553 A1 | 3/2005 | Nilsson et al. | |
| 2011/0166237 A1 * | 7/2011 | Haldavanekar et al. | 514/653 |

FOREIGN PATENT DOCUMENTS

| | | |
|---|---|---|
| IN | 1179MUM2012 | 4/2012 |
| WO | 0048587 A1 | 8/2000 |
| WO | 0170198 A1 | 9/2001 |
| WO | 0178745 A1 | 10/2001 |
| WO | 02083113 A2 | 10/2002 |
| WO | 2004028545 A1 | 4/2004 |
| WO | 2011045429 A1 | 4/2011 |
| WO | 2011136753 A1 | 11/2011 |
| WO | 2013153349 A2 | 10/2013 |
| WO | 2013153349 A3 | 10/2013 |

OTHER PUBLICATIONS

Shur et al., Pharmaceutical Research, 2009, 26(12): 2657-2666.*
Cazzola et al. publication, British Journal of Pharmacoloy, 2011, 163:4-17.*
Busse et al., Thorax, 2012, 67(1):35-41.*
Zhong et al. publication, Curr Med Res Opin, 2012, 282): 257-65.*
Paul King. International Journal of Chronic Obstructive Pulmonary Disease, 2008, 3(3): 385-391.*
Foreign communication from the priority application—International Search Report and Written Opinion, PCT/GB2013/000161, Dec. 4, 2013, 12 pages.
Foreign communication from the priority application—International Preliminary Report on Patentability, PCT/GB2013/000161, Oct. 14, 2014, 9 pages.

* cited by examiner

*Primary Examiner* — Rei-Tsang Shiao
(74) *Attorney, Agent, or Firm* — Conley Rose, P.C.; Rodney B. Carroll

(57) ABSTRACT

The present invention relates to a pharmaceutical composition comprising arformoterol and fluticasone furoate (preferably for once daily administration), to a process for preparing such a composition and to the use of such a composition for the treatment and/or prevention of respiratory, inflammatory or obstructive airway disease.

20 Claims, No Drawings

PHARMACEUTICAL COMPOSITION

CROSS REFERENCE TO RELATED APPLICATIONS

This application is a filing under 35 U.S.C. 371 of International Application No. PCT/GB2013/000161 filed Apr. 10, 2013, entitled "Pharmaceutical Composition," which claims priority to Indian Patent Application No. 1179/MUM/2012 filed Apr. 11, 2012, which applications are incorporated by reference herein in their entirety.

FIELD OF INVENTION

The present invention relates to pharmaceutical compositions for inhalation comprising an inhaled corticosteroid and a β-agonist, and processes for preparing the compositions. Furthermore the invention relates to the use of said composition in the treatment and/or prevention of respiratory, inflammatory or obstructive airway disease and methods of treatment employing the same.

BACKGROUND OF INVENTION

Asthma is a major cause of chronic morbidity and mortality, with an estimated 300million affected individuals worldwide and 250,000 annual deaths attributed to the disease. People of all ages in most countries are affected by this chronic disease.

Asthma is a chronic inflammatory disorder of the airways associated with airway hyper responsiveness that leads to recurrent episodes of wheezing, breathlessness, chest tightness, and coughing. An increased inflammatory response is a major part of the pathophysiology of acute asthma and regular preventive treatment of the same is very important.

Chronic obstructive pulmonary disease (COPD) is a severe respiratory condition that is increasing in prevalence worldwide. In India, the estimated prevalence is about 12.36 million.

Chronic obstructive pulmonary disease (COPD) is a preventable and treatable disease state characterized by air flow limitation that is not fully reversible. The airflow obstruction is usually progressive and associated with an abnormal inflammatory response of the lungs to noxious particles or gases, primarily caused by cigarette smoking. Although COPD affects the lungs it also produces significant systemic consequences. COPD is associated with mucus hyper secretion, emphysema and bronchiolitis.

Therapy for the treatment or prevention of COPD and asthma currently includes the use of bronchodilators and steroids.

More specifically asthma, COPD and other related disorders have been known to be treated with $\beta_2$-agonists as they provide a bronchodilator effect, resulting in relief from the symptoms of breathlessness. $\beta_2$-agonists can be short acting for immediate relief or long acting for long term prevention of asthma symptoms.

Long acting $\beta_2$-agonists improve lung function, reduce symptoms and protect against exercise-induced dyspnea in patients with asthma and COPD. Long acting $\beta_2$-agonists induce bronchodilation by causing prolonged relaxation of airway smooth muscle. In addition to prolonged bronchodilation, long acting $\beta_2$-agonists (LABAs) exert other effects such as inhibition of airway smooth-muscle cell proliferation and inflammatory mediator release as well as non smooth-muscle effects such as stimulation of mucociliary transport, cytoprotection of the respiratory mucosa and attenuation of neutrophil recruitment and activation.

Further, use of a long acting $\beta_2$-agonist reduces the frequency of drug administration.

Currently available long acting $\beta_2$-agonists (LABAs) include salmeterol and formoterol.

Even though it is known that $\beta_2$-agonists provide a symptomatic relief in bronchoconstriction and another component of asthma, which is inflammation, requires separate treatment such as steroid. Most of the inhaled corticosteroids need to be administered in multiple dosage regimens.

Corticosteroids exhibit inhibitory effects on inflammatory cells and inflammatory mediators involved in the pathogenesis of respiratory disorders. Treatment with a corticosteroid/glucocorticoid is considered one of the most potent and effective therapies currently available for persistent asthma.

But the use of corticosteroids has been limited due to potential side effects. The side effects that are normally feared with corticosteroids include suppression of the Hypothalamic-Pituitary-Adrenal (HPA) axis, effects on bone growth in children and on bone density in the elderly, ocular complications (cataract formation and glaucoma) and skin atrophy.

Currently available corticosteroids include beclomethasone, budesonide, fluticasone, mometasone, ciclesonide and triamcinolone.

Currently, there are several approved combinations of long-acting β-agonist (LABA) and inhaled corticosteroid (ICS). Some of these approved combinations for the treatment of asthma and chronic obstructive pulmonary disease (COPD) are salmeterol/fluticasone propionate (Advair diskus, Advair HFA), and formoterol fumarate dihydrate/budesonide (Symbicort).

Combination therapy of a long-acting β-agonist (LABA) with an inhaled corticosteroid (ICS) improves pulmonary efficiency, reduces inflammatory response and provides symptomatic relief as compared to higher doses of inhaled corticosteroid (ICS) alone in patients affected by respiratory disorders such as asthma and COPD.

Additionally it simplifies the therapy, reduces the cost and also provides control of respiratory disorders.

U.S. Pat. No. 6,030,604 discloses a dry powder composition comprising glucocorticoids and $\beta_2$-agonist.

WO0178745 discloses compositions containing a combination of formoterol and fluticasone propionate.

U.S. Pat. No. 7,172,752 discloses inhalation particles comprising a combination of a $\beta_2$-agonist and a glucocorticosteroid in a predetermined and constant ratio.

WO02083113 discloses pharmaceutical compositions comprising formoterol and a steroidal anti-inflammatory agent in a pharmacologically suitable fluid.

WO2004028545 discloses a combination of a long-acting $\beta_2$-agonist and a glucocorticosteroid in the treatment of fibrotic diseases.

US 2005053553 discloses methods for administration by inhalation of a metered dry powder having combined doses of formoterol and fluticasone.

Further, none of the above mentioned prior arts disclose a specific combination of Arformoterol and Fluticasone furoate Most of the available combinations of a long-acting β-agonist (LABA) with inhaled corticosteroid (ICS) have to be administered twice daily.

Even from the patient compliance point of view, the treatment requires for the patient to comply with different dosage regimens, different frequencies of administration etc.

Efforts to improve compliance have been aimed at by simplifying the medication packaging, providing effective medication reminders, improving patient education and limiting the number of medications prescribed simultaneously.

Hence, there still remains a need to formulate a pharmaceutical composition which simplifies the dosage regimen by administering an effective combination of arformoterol and fluticasone furoate for the treatment of respiratory disorders.

OBJECT OF THE INVENTION

The object of the present invention is to provide a pharmaceutical composition comprising a long-acting β-agonist (LABA) and an inhaled corticosteroid (ICS) for administration in the prevention or treatment of respiratory, inflammatory or obstructive airway disease.

Another object of the present invention is to provide a pharmaceutical composition comprising a long-acting β-agonist (LABA) and an inhaled corticosteroid (ICS) for once daily administration for the prevention or treatment of respiratory, inflammatory or obstructive airway disease.

Yet another object of the present invention is to provide a process for preparing the pharmaceutical composition comprising a long-acting β-agonist (LABA) and an inhaled corticosteroid (ICS) for administration in the prevention or treatment of respiratory, inflammatory or obstructive airway disease.

A further object of the present invention is to provide a method for the treatment or prevention of asthma, COPD or a related respiratory disorder, which method comprises administering a pharmaceutical composition comprising a long-acting β-agonist (LABA) and an inhaled corticosteroid (ICS).

SUMMARY OF THE INVENTION

According to one aspect of the present invention, there is provided a pharmaceutical composition comprising arformoterol and fluticasone furoate.

According to another aspect of the present invention, there is provided a pharmaceutical composition comprising arformoterol and fluticasone furoate for once daily administration.

According to yet another aspect of the present invention, there is provided a process for preparing a pharmaceutical composition, said process comprising combining arformoterol and fluticasone furoate, optionally with one or more pharmaceutically acceptable carriers and/or excipients.

According to still another aspect of the present invention, there is provided a method for the treatment or prevention of asthma, chronic obstructive pulmonary disease (COPD) or a related disorder, said method comprising administration of a pharmaceutical composition according to the present invention to a patient in need thereof.

According to a further aspect of the present invention there is provided the pharmaceutical composition of the present invention for use in the treatment or prevention of asthma, COPD or a related disorder.

According to a yet further aspect of the present invention there is provided the use of a pharmaceutical composition of the present invention for the treatment or prevention of asthma, chronic obstructive pulmonary disease (COPD) or a related disorder.

DETAILED DESCRIPTION OF THE INVENTION

Drug therapy with a long-acting β-agonist (LABA) and inhaled corticosteroid (ICS) has been recommended for the prevention or treatment of respiratory, inflammatory or obstructive airway disease such as asthma and chronic obstructive pulmonary disease (COPD).

Also, there is a need to simplify the various different dosage regimens as well as the different frequencies of drug administration.

Further selecting a combination of a long-acting $\beta_2$-agonist (LABA) and an inhaled corticosteroid (ICS) is critical since both drugs should be capable of being administered once daily. A treatment method where a long-acting $\beta_2$-agonist (LABA) is required to be administered once daily and an inhaled corticosteroid (ICS) is required to be administered twice daily will not be useful since the purpose of once a day treatment is defeated.

Further there is a need to formulate a composition which can be administered once daily for the prevention of conditions that respond to or are prevented, ameliorated or eliminated by the administration of long-acting β-agonists (LABA) and inhaled corticosteroids (ICS).

It has been surprisingly found that arformoterol in combination with fluticasone furoate provides relief from respiratory disorders while simultaneously reducing the frequency of dosage administration.

The present invention thus provides a novel combination for inhalation comprising arformoterol in combination with fluticasone furoate for the prevention or treatment of respiratory, inflammatory or obstructive airway disease while simultaneously reducing the frequency of dosage administration.

The term "arformoterol" is used in a broad sense to include not only "arformoterol" per se but also its pharmaceutically acceptable salts, pharmaceutically acceptable solvates, pharmaceutically acceptable hydrates, pharmaceutically acceptable enantiomers, pharmaceutically acceptable derivatives, pharmaceutically acceptable esters, pharmaceutically acceptable polymorphs, pharmaceutically acceptable prodrugs, pharmaceutically acceptable complex, pharmaceutically acceptable co-crystals etc. Arformoterol salts include acid addition salts such as acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid and p-toluenesulfonic. Preferably the arformoterol salt used in the present invention is arformoterol tartrate or arformoterol fumarate, especially arformoterol fumarate dihydrate.

Arformoterol is the active (R,R)-enantiomer of formoterol. It has a rapid onset and a longer duration of action. Further, Arformoterol has two-fold greater potency than racemic formoterol (which contains both the (S,S) and (R,R) enantiomers). Arformoterol seems to have little or no effect on $\beta_1$-adrenergic receptors.

The term "fluticasone furoate" is used in broad sense to include not only "fluticasone furoate" per se but also its pharmaceutically acceptable salts, pharmaceutically acceptable solvates, pharmaceutically acceptable enantiomers, pharmaceutically acceptable hydrates, pharmaceutically acceptable derivatives, pharmaceutically acceptable polymorphs, pharmaceutically acceptable prodrugs, pharmaceutically acceptable complex, pharmaceutically acceptable co-crystals etc.

Fluticasone is currently available as a furoate ester and propionate ester. Fluticasone furoate is a corticosteroid which substantially overcomes the potential side effects that are generally produced by the use of conventional corticosteroids. Moreover fluticasone furoate exhibits a 1.7 times higher binding affinity for the human glucocorticoid receptor as compared to that of fluticasone propionate.

Fluticasone furoate has a longer duration of action with an elimination half life of 15.1 hrs. Arformoterol has a longer duration of action and also exhibits a faster onset of action.

Fluticasone furoate and Arformoterol mainly act on two different components of asthma exhibiting a complimentary action. Chronic inflammation which is commonly associated with asthma is managed by fluticasone furoate while other aspects of asthma, such as abnormalities in bronchial smooth muscle are improved, by arformoterol.

Hence, the combination of fluticasone furoate with arformoterol provides a novel combination which has the convenience of once daily administration for patients of asthma and COPD.

Further a rapid onset of the effect of the combination due to arformoterol may increase the patient's confidence in the treatment and subsequently improve compliance to therapy.

According to the present invention, a single dose may comprise from about 2 mcg to about 10 mcg of arformoterol, preferably from about 3 mcg to about 9 mcg. A single dose may comprise about 3 mcg, about 5 mcg, about 7 mcg or about 9 mcg of arformoterol.

According to the present invention, a single dose may comprise from about 25 mcg to about 800 mcg of fluticasone furoate, preferably from about 50 mcg to about 400 mcg. A single dose may comprise about 27.5 mcg, about 50 mcg, about 100 mcg, about 125 mcg, about 200 mcg, about 250 mcg or about 400 mcg.

In embodiments in which the composition of the present invention is administered once a day, a single dose may provide the daily dose. Alternatively, the daily dose may comprise multiple doses of the composition, e.g. two doses, which can be taken at the same time if administered once a day or which can be taken at different times if administered more than once a day.

In embodiments in which a single dose provides a single daily dose, a single daily dose may comprise 5 mcg fluticasone furoate and 50 mcg arformoterol, 5 mcg fluticasone furoate and 125 mcg arformoterol, or 10 mcg fluticasone furoate and 250 mcg arformoterol.

The molar ratio of arformoterol to fluticasone furoate in the composition of the invention is preferably from about 1:10 to 1:100, preferably from 1:15 to 1:70.

The pharmaceutical composition may be in a form suitable for administration as a single medicament.

The pharmaceutical compositions of the present invention may comprise arformoterol and fluticasone furoate with one or more pharmaceutically acceptable excipients.

The pharmaceutical compositions of the present invention may be administered by any suitable method used for delivery of the drugs to the respiratory tract. The compositions of the present invention may thus be in a form suitable for inhalation. Hence the pharmaceutical composition may be formulated as a composition for inhalation from metered dose inhalers (MDI), dry powder inhalers (DPI), nebulisers and the like; or the pharmaceutical composition may be formulated as a composition for inhalation in the form of a nasal spray, nasal drops, respules, insufflation powders and the like. A "respule" is a dosage form suitable for use with a nebuliser; a respule is an ampoule containing a drug in liquid form. Respules, nasal sprays and nasal drops may contain the pharmaceutical compositions of the present invention in the form of an inhalation solution or inhalation suspension.

The various dosage forms according to the present invention may comprise carriers/excipients suitable for formulating the same.

The metered dose inhalers, according to the present invention, may comprise one or more pharmaceutically acceptable excipients as HFC/HFA propellants, co-solvents, bulking agents, non volatile component, buffers/pH adjusting agents, surfactants, preservatives, complexing agents, or combinations thereof.

Propellants are those which, when mixed with the cosolvent(s), form a homogeneous propellant system in which a therapeutically effective amount of the medicament can be dissolved. The HFC/HFA propellant must be toxicologically safe and must have a vapor pressure which is suitable to enable the medicament to be administered via a pressurized MDI.

According to the present invention the HFC/HFA propellants may comprise, one or more of 1,1,1,2-tetrafluoroethane (HFA-134(a)) and 1,1,1,2,3,3,3,-heptafluoropropane (HFA-227), HFC-32 (difluoromethane), HFC-143(a) (1,1,1-trifluoroethane), HFC-134 (1,1,2,2-tetrafluoroethane), and HFC-152a (1,1-difluoroethane) and the like or combinations thereof and such other propellants which may be known to the person having a skill in the art.

Co-solvent is any solvent which is miscible in the composition in the amount desired and which, when added provides a composition in which the medicament can be dissolved. The function of the co-solvent is to increase the solubility of the medicament and the excipients in the composition.

According to the present invention the co-solvent may comprise one or more of, $C_2$-$C_6$ aliphatic alcohols, such as, but not limited to, ethyl alcohol and isopropyl alcohol; glycols such as but not limited to propylene glycol, polyethylene glycols, polypropylene glycols, glycol ethers, and block copolymers of oxyethylene and oxypropylene; and other substances, such as but not limited to glycerol, polyoxyethylene alcohols, and polyoxyethylene fatty acid esters; hydrocarbons such as but not limited to n-propane, n-butane, isobutane, n-pentane, iso-pentane, neo-pentane, and n-hexane; and ethers such as but not limited to diethyl ether and the like or combinations thereof.

Suitable surfactants may be employed in the aerosol solution composition of the present invention which may serve to stabilize the solution composition and improve the performance of valve systems of the metered dose inhaler.

According to the present invention the surfactant may comprise one or more ionic and/or non-ionic surfactant, but not limited to oleic acid, sorbitan trioleate, lecithin, isopropylmyristate, tyloxapol, polyvinylpyrrolidone, polysorbates such as polysorbate 80, vitamin E-TPGS, and macrogol hydroxystearates such as macrogol-15-hydroxystearate and the like or combinations thereof.

Non-volatile component is all the suspended or dissolved constituents that would be left after evaporation of the solvent.

According to the present invention, the non-volatile component may comprise one or more of saccharides, including monosaccharides such as but not limited to glucose, arabinose and disaccharides such as lactose, maltose; oligosaccharides and polysaccharides such as but not limited to dextrans; polyalcohols such as but not limited to glycerol, sorbitol, mannitol, xylitol and the like or combinations thereof; and/or salts such as but not limited to potassium chloride, magnesium chloride, magnesium sulphate, sodium chloride, sodium citrate, sodium phosphate, sodium hydrogen phosphate, sodium hydrogen carbonate, potassium citrate, potassium phosphate, potassium hydrogen phosphate, potassium hydrogen carbonate, calcium carbonate and calcium chloride and the like or combinations thereof.

Suitable bulking agents may be employed in metered dose inhalation composition of the present invention.

According to the present invention, the bulking agent may comprise one or more of saccharides, including monosaccharides, disaccharides, polysaccharides and sugar alcohols such as arabinose, glucose, fructose, ribose, mannose, sucrose, terhalose, lactose, maltose, starches, dextran or mannitol and the like or combinations thereof.

Suitable buffers or pH adjusting agents may be employed in the metered dose inhalation composition of the present invention.

According to the present invention, the buffer or the pH adjusting agent may comprise one or more of organic or inorganic acids such as but not limited to citric acid, ascorbic acid, hydrochloric acid, sulfuric acid, nitric acid, or phosphoric acid and the like or combinations thereof.

Suitable preservatives may be employed in the aerosol solution composition of the present invention to protect the composition from contamination with pathogenic bacteria.

According to the present invention, the preservative may comprise one or more of benzalkonium chloride, benzoic acid, benzoates such as sodium benzoate and the like or combinations thereof and such other preservatives which may be known to the person having a skill in the art.

Suitable complexing agents may be employed in the aerosol solution composition of the present invention which is capable of forming complex bonds.

According to the present invention, the complexing agent may comprise one or more of but not limited to sodium EDTA or disodium EDTA and the like or combinations thereof.

The pharmaceutical composition of the present invention may also be administered by a dry powder inhaler (DPI).

The pharmaceutically acceptable excipients suitable for dry powder inhalation according to the present invention may be selected from suitable carriers which include but are not limited to sugars such as glucose, saccharose, lactose and fructose, starches or starch derivatives, oligosaccharides such as dextrins, cyclodextrins and their derivatives, polyvinylpyrrolidone, alginic acid, tylose, silicic acid, cellulose, cellulose derivatives (for example cellulose ether), sugar alcohols such as mannitol or sorbitol, calcium carbonate, calcium phosphate, etc. lactose, lactitol, dextrates, dextrose, maltodextrin, saccharides including monosaccharides, disaccharides, polysaccharides; magnesium stearate, glycine, sodium citrate, sugar alcohols such as arabinose, ribose, mannose, sucrose, trehalose, maltose, dextran and the like or combinations thereof.

The pharmaceutical composition of the present invention may be administered using a nebuliser as well.

Nebulisation is a safe therapy to deliver or deposit medications directly into the respiratory tract and hence achieve higher drug concentrations. Nebulisation is easy to use and does not require co-ordination or much effort. It also works much more rapidly than medicines taken by mouth.

In embodiments in which the pharmaceutical composition is formulated for inhalation in the form of a nasal spray, nasal drops or respules, the composition may comprise suitable excipients such as wetting agents, osmotic agents, tonicity agents, pH regulators, buffering agents, complexing agents and the like or combinations thereof in a suitable vehicle such as, but not limited to water, saline and the like.

Tonicity agents, that may be used, comprise sodium chloride, potassium chloride, zinc chloride, calcium chloride and the like or combinations thereof. Other tonicity agents may also include, but are not limited to, mannitol, glycerol, and dextrose and the like or combinations thereof.

The pH may be adjusted by the addition of pharmacologically acceptable acids. Pharmacologically acceptable inorganic acids or organic acids may be used for this purpose. Examples of preferred inorganic acids are selected from the group consisting of hydrochloric acid, hydrobromic acid, nitric acid, sulphuric acid and phosphoric acid. Examples of particularly suitable organic acids are selected from the group consisting of ascorbic acid, citric acid, malic acid, tartaric acid, maleic acid, succinic acid, fumaric acid, acetic acid, formic acid and propionic acid and the like or combinations thereof.

Complexing agents according to the present invention may comprise edetic acid (EDTA) or one of the known salts thereof, e.g. sodium EDTA or disodium EDTA dihydrate (sodium edetate) and the like or combinations thereof.

Anti-microbial preservative agent may be added for multi-dose packages.

The compositions according to the present invention may be packed in suitable containers provided with means of enabling the delivery/deposition of the contained composition to the respiratory tract.

The powder for inhalation intended to be delivered by DPI may either be encapsulated in capsules of gelatin or hydroxypropyl methyl cellulose (HPMC) or in blisters or alternatively, a reservoir may be filled with the dry powder either in a single dose or multi-dose dry powder inhalation device.

Alternatively, the powder for inhalation intended to be delivered by DPI may be suspended in a suitable liquid vehicle and packed in an aerosol container along with suitable propellants or mixtures thereof.

Further, the powder for inhalation intended to be delivered by DPI may also be dispersed in a suitable gas stream to form an aerosol composition.

The MDI composition according to the present invention may be packed in plain aluminium cans or SS (stainless steel) cans. Some aerosol drugs tend to adhere to the inner surfaces, i.e., walls of the cans and valves, of the MDI. This can lead to the patient getting significantly less than the prescribed amount of the active agent upon each activation of the MDI. Coating part or all of the inner surface of the container with a suitable polymer can reduce this adhesion problem. Suitable coatings include fluorocarbon copolymers such as FEP-PES (fluorinated ethylene propylene and polyethersulphone) and PFA-PES (perfluoroalkoxyalkane and polyethersulphone), epoxy and ethylene. Alternatively, the inner surfaces of the cans may be anodized, plasma treated or plasma coated.

It may be well acknowledged to a person skilled in the art that the said pharmaceutical composition, according to the present invention, may further comprise one or more active(s) selected from anticholinergics, antihistamines, antiallergics or leukotriene antagonist and the like or combinations thereof or their pharmaceutically acceptable salts, solvates, tautomers, derivatives, enantiomers, isomers, hydrates, prodrugs or polymorphs thereof.

The present invention also provides a process to manufacture the compositions according to the present invention.

The present invention provides a process of preparing a metered dose inhalation composition. The process comprises combining a pharmaceutically acceptable carrier or excipient with the actives and the propellant and providing the composition in precrimped cans.

The present invention also provides a process of preparing a dry powder inhalation composition. The process comprises combining a pharmaceutically acceptable carrier or excipient with the actives and providing the composition in a dry powder inhaler device.

The present invention also provides a method for the treatment or prevention of asthma, COPD or a related disorder. The method of treatment comprises administration of a pharmaceutical composition according to the present invention to a patient in need thereof. The patient may be a mammal, such as a human.

The following examples are for the purpose of illustration of the invention only and are not intended in any way to limit the scope of the present invention.

EXAMPLE 1

| Sr. No. | Ingredients | Qty/spray |
|---|---|---|
| 1. | Fluticasone Furoate | 50 mcg |
| 2. | Arformoterol tartrate | 3 mcg |
| 3. | HFA134A/HFA227 | q. s. |

Process:
1) Fluticasone Furoate and Arformoterol tartrate were homogenized with Part quantity of HFA.
2) The suspension obtained in step 1 was transferred to the mixing vessel where remaining quantity of HFA was added.
3) The resulting suspension was mixed, recirculated and filled into a pre-crimped Aluminium can.

EXAMPLE 2

| Sr. No. | Ingredients | Qty/spray |
|---|---|---|
| 1. | Fluticasone Furoate | 50 mcg |
| 2. | Arformoterol tartrate | 3 mcg |
| 3. | Lactose | 100% of the drug |
| 4. | HFA134A/HFA227 | q. s. |

Process:
1) Fluticasone Furoate and Arformoterol tartrate were homogenized with lactose and part quantity of HFA.
2) The suspension obtained in step 1 was transferred to the mixing vessel where remaining quantity of HFA was added
3) The resulting suspension was mixed, recirculated and filled into a pre-crimped Aluminium can.

EXAMPLE 3

| Sr. No. | Ingredients | Qty/spray |
|---|---|---|
| 1. | Fluticasone Furoate | 50 mcg |
| 2. | Arformoterol tartrate | 3 mcg |
| 3. | Ethanol | 1-2% of total formulation |
| 4. | Oleic acid | 0.02-5% of the API |
| 5. | HFA134a/HFA227 | q. s. |

Process:
1) Oleic acid was dissolved in Ethanol. Arformoterol tartrate was homogenized with part quantity of HFA and transferred to the mixing vessel
2) The solution of oleic acid and ethanol was homogenized with Fluticasone Furoate and part quantity of HFA
3) The suspension obtained in step 2 was transferred to the mixing vessel where remaining quantity of HFA was added 4) The resulting suspension was then mixed, recirculated and filled into a pre-crimped Aluminium can.

EXAMPLE 4

| Sr. No. | Ingredients | Qty/Unit (mg) |
|---|---|---|
| 1. | Arformoterol | 0.0088 |
| 2. | Fluticasone Furoate | 0.1000 |
| 3. | Lactose monohydrate | 24.8912 |
| | Total | 25.000 |

Process:
1) Sifted lactose was co-sifted with Arformoterol and fluticasone furoate.
2) The mixture obtained in step (1) was blended.

EXAMPLE 5

| Sr. No. | Ingredients | Qty/Unit (mg) |
|---|---|---|
| 1. | Arformoterol | 0.0088 |
| 2. | Fluticasone Furoate | 0.2000 |
| 3. | Lactose monohydrate | 24.7912 |
| | Total | 25.000 |

Process:
1) Sifted lactose was co-sifted with Arformoterol and fluticasone furoate.
2) The mixture obtained in step (1) was blended.

EXAMPLE 6

| Sr. No. | Ingredients | Qty/Unit (mg) |
|---|---|---|
| 1. | Arformoterol | 0.0088 |
| 2. | Fluticasone Furoate | 0.4000 |
| 3. | Lactose monohydrate | 24.5912 |
| | Total | 25.000 |

Process:
1) Sifted lactose was co-sifted with Arformoterol and fluticasone furoate.
2) The mixture obtained in step (1) was blended.

It will be readily apparent to one skilled in the art that varying substitutions and modifications may be made to the invention disclosed herein without departing from the spirit of the invention. Thus, it should be understood that although the present invention has been specifically disclosed by the preferred embodiments and optional features, modification and variation of the concepts herein disclosed may be resorted to by those skilled in the art, and such modifications and variations are considered to be falling within the scope of the invention.

It is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It must be noted that, as used in this specification and the appended claims, the singular forms "a," "an" and "the" include plural references unless the context clearly dictates otherwise. Thus, for example, reference to "an excipient" includes a single excipient as well as two or more different excipients, and the like.

The invention claimed is:

1. A pharmaceutical composition comprising arformoterol and fluticasone furoate.

2. The pharmaceutical composition according to claim 1, wherein a single dose of said composition comprises from about 2 mcg to about 10 mcg of arformoterol.

3. The pharmaceutical composition according to claim 1, wherein a single dose of said composition comprises from about 25 mcg to about 800 mcg of fluticasone furoate.

4. The pharmaceutical composition according to claim 1, wherein the molar ratio of arformoterol to fluticasone furoate is from about 1:10 to 1:100.

5. The pharmaceutical composition according to claim 1, further comprising one or more pharmaceutically acceptable carriers and/or excipients.

6. The pharmaceutical composition according to claim 1, wherein the composition is in a form suitable for inhalation.

7. The pharmaceutical composition according to claim 6, formulated as a composition for inhalation in the form of a nasal spray, nasal drops, respules an insufflation powder or inhalation from a metered dose inhaler (MDI), a dry powder inhaler (DPI) or a nebulizer.

8. The pharmaceutical composition according to claim 1, wherein the composition is in a form suitable for use in a metered dose inhaler (MDI).

9. The pharmaceutical composition according to claim 8, further comprising a propellant.

10. The pharmaceutical composition according to claim 8, further comprising an excipient selected from a co-solvent, an antioxidant, a surfactant, a bulking agent, a pH adjusting agent and a lubricant or combinations thereof.

11. The pharmaceutical composition according to claim 1, wherein the composition is in a form suitable for use in a dry powder inhaler (DPI).

12. The pharmaceutical composition according to claim 11, further comprising at least one pharmaceutically acceptable carrier suitable for use in dry powder inhalation formulations.

13. The pharmaceutical composition according to claim 12, wherein said carrier includes a saccharide and/or a sugar alcohol or combinations thereof.

14. The pharmaceutical composition according to claim 1, wherein the composition is in a form suitable for use in a nasal spray, nasal drops or respules.

15. The pharmaceutical composition according to claim 14, further comprising an excipient selected from a wetting agent, an osmotic agent, a tonicity agent, a pH regulator, a buffering agent and a complexing agent or combinations thereof, provided in a pharmaceutically acceptable vehicle.

16. The pharmaceutical composition according to claim 1, wherein the composition is in a form suitable for once daily administration.

17. The pharmaceutical composition according to claim 1, further comprising one or more additional actives selected from anticholinergics, antihistamines, antialiergics or leukotriene antagonists.

18. A process for preparing a pharmaceutical composition according to claim 1, comprising combining arformoterol and fluticasone furoate, optionally with one or more pharmaceutically acceptable carriers and/or excipients.

19. A method for treatment of asthma, chronic obstructive pulmonary disease (COPD) or a related disorder, comprising administering to a human a pharmaceutical composition according to claim 1.

20. A method utilizing the pharmaceutical composition according to claim 1 for the treatment of asthma, chronic obstructive pulmonary disease (COPD) or a related disorder.

* * * * *